United States Patent [19]
Newell et al.

[11] Patent Number: 6,113,892
[45] Date of Patent: *Sep. 5, 2000

[54] COMPOSITIONS FOR CLEANSING, CONDITIONING AND MOISTURIZING HAIR AND SKIN

[75] Inventors: Gerald Patrick Newell, Hoffman Estates; Teresa Cuasay Manuel, Lake in the Hills, both of Ill.

[73] Assignee: Helene Curtis, Inc., Chicago, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/997,684

[22] Filed: Dec. 23, 1997

[51] Int. Cl.$^7$ .............................. A61K 7/075; A61K 7/48
[52] U.S. Cl. .................... 424/70.19; 424/70.12; 424/70.17; 424/401
[58] Field of Search .............. 424/70.12, 70.17, 424/70.19, 401

[56] References Cited

U.S. PATENT DOCUMENTS

| | | |
|---|---|---|
| 3,929,678 | 12/1975 | Laughlin et al. . |
| 4,152,416 | 5/1979 | Spitzer et al. . |
| 4,717,498 | 1/1988 | Maxon . |
| 4,931,271 | 6/1990 | Lang et al. . |
| 5,085,857 | 2/1992 | Reid et al. . |
| 5,236,710 | 8/1993 | Guerrero et al. . |
| 5,306,434 | 4/1994 | Schueller ................................ 252/8.8 |
| 5,336,497 | 8/1994 | Guerrero et al. . |
| 5,356,438 | 10/1994 | Kim ............................................ 8/405 |
| 5,683,683 | 11/1997 | Scafidi . |

FOREIGN PATENT DOCUMENTS

| | | |
|---|---|---|
| 659405 | 6/1995 | European Pat. Off. . |
| 738509 | 10/1996 | European Pat. Off. . |

*Primary Examiner*—Jyothsna Venkat
*Attorney, Agent, or Firm*—Matthew Boxer

[57] ABSTRACT

The present invention relates to compositions for cleansing, conditioning, and moisturizing the skin and hair which comprise:

i) a high foaming anionic surfactant;
ii) a polymeric cationic conditioning agent;
iii) a silicone copolyol sulfosuccinate;
iv) an emollient; and
v) water.

8 Claims, No Drawings

COMPOSITIONS FOR CLEANSING, CONDITIONING AND MOISTURIZING HAIR AND SKIN

FIELD OF THE INVENTION

The present invention is related to compositions which have multiple cleansing, conditioning and moisturizing functions. That is, the present invention relates to compositions for cleansing, conditioning and moisturizing hair and skin. Compositions of the invention can be called shampoo bodywash compositions.

RELATED ART

Patents which relate to the present invention are as follows:

DE 4,404,790 discloses a multifunctional cosmetic preparation useful as a shampoo, hair conditioner, shower cosmetic, cream and hair care agent. The preparation comprises a) di-Na lauryl alcohol polyglycol ether sulfosuccinate, Na Mg and/or $NH_4$ lauryl sulphate, Na lauryl sulphoacetate and or lauryl polyglucose b) a combination of (bi)Ca salt of an albumin/fatty acid condensate and bi(d-Me carboxymethyl-coconut fatty acid amidoammonium betaine or a polysiloxane/polyorganobetaine copolymer c)0 N-lauryl-L-glutamic acid dissolved in lauryl polyglycoside ether d) cationic guar e) dihydrogenated tallow phthalamide and f auxiliaries and carriers.

EP 659,405 discloses cosmetic compositions for conditioning the hair or skin containing a combination of a quaternary polyammonium polymer and a di-alkyl-dialkyl ammonium copolymer.

U.S. Pat. No. 4,931,271 discloses cosmetic compositions for treating hair or skin which contain an effective amount of chitosan derivatives to facilitate skin moistening and to give skin a soft feel.

EP 0,738,509 A2 discloses a combination cleansing and conditioning composition which comprises an anionic surfactant, an amphoteric surfactant, a suspending agent, and insoluble particles bearing an effective amount of oily water insoluble skin or hair conditioning agents, the particles being readily able to deliver the conditioning agent when the particle is abraded against the skin or hair during cleansing.

U.S. Pat. No. 5,085,857 discloses a shampoo composition containing surfactant together with cationic guar and an insoluble nonvolatile silicone present as emulsified particles having an average particle size below two microns.

Presently, people use a hair shampoo, a hair conditioner, and a bodywash and a skin moisturizer, that is to say four different products, when cleansing, conditioning, and moisturizing the skin and hair. An object of the present invention is to provide a single composition that can clean, condition, and moisturize the skin and hair. As such, the composition of the invention allows consumers to have fewer products to buy, to have fewer products in the shower stall, to save time in the cleansing, conditioning, and moisturizing process, and to have fewer products to carry when traveling.

Anionic surfactant-based skin cleansers or soaps effectively cleanse the skin, but leave the skin in a cosmetically unsatisfactory state because they remove oils that are naturally present on the surface of the skin. Accordingly, skin that has been repeatedly washed with an anionic surfactant-based skin cleanser or soap, often require treatment with a skin-conditioner composition to replenish the oil and moisture removed from the skin. The compositions of the present invention avoid the necessity of this two step process because they are conditioners as well as cleansers.

Anionic shampoos effectively clean hair, but leave it in an unsatisfactory condition, that is, they leave it difficult to comb. As a result, use of a conditioner is required after using such shampoos. By contrast, use of compositions of the invention avoids the need to use a conditioner afterwards, since compositions of the invention leave hair in good condition.

SUMMARY OF THE INVENTION

The present invention relates to compositions for cleansing, conditioning, and moisturizing the skin and hair which comprise:
i.) a high foaming anionic surfactant;
ii) a polymeric cationic conditioning agent;
iii) a silicone copolyol sulfosuccinate;
iv) an emollient; and
v.) water The present invention also relates to a method for cleansing, conditioning, and moisturizing the skin and hair which comprises placing some of the composition of the invention into the hands, lathering the skin and/or hair and rinsing off the lather with water.

Alternatively, the compositions of the invention may be placed, for example, on a pouf, a wash cloth, or a natural or synthetic sponge, and lathered either in the hair or on the skin or both. Then the lather is rinsed off with water.

DETAILED DESCRIPTION OF THE PREFERRED EMBODIMENTS

As used herein, and unless otherwise indicated, %, means weight per cent of the composition. Unless otherwise indicated, when ingredients or materials are given in weight per cents, said ingredients or materials are given in a 100% active basis.

All of the starting materials used to make compositions of the invention are either known or can be made by known methods.

There has now been identified a composition which has excellent properties for cleansing, conditioning, and moisturizing the skin and hair. The composition is based upon silicone copolyol sulfosuccinate compounds in combination with an anionic surfactant; a polymeric cationic conditioning agent and an emollient.

An important component of the compositions of the present invention is that of a high foaming anionic surfactant.

Another important component of the compositions of the present invention is that of a polymeric cationic conditioning agent.

Another important component of compositions of the invention is a silicone copolyol sulfosuccinate as set forth in U.S. Pat. No. 5,085,857 which is hereby incorporated by reference. There may also be present in compositions of the invention, dimethicone copolyol succinates as set forth in U.S. Pat. No. 4,717,498 which is hereby incorporated by reference.

Another important component of the compositions of the present invention is an emollient. Emollients are used to soften and improve the appearance of skin.

Another important component of the compositions of the present invention is water.

An optional component of the compositions of the invention is that of an amphoteric surfactant. Amphoteric surfactants suitable for use in the compositions of the present invention are described in U.S. Pat. No. 5,336,497 and U.S. Pat. No. 5,236,710 which are hereby incorporated by reference.

The compositions of the invention also optionally comprise an insoluble, non-volatile silicone, which may be one or more polyalkyl siloxanes, one or more polyaryl siloxanes, or mixtures thereof.

Suitable polyalkyl siloxanes include polydimethyl siloxanes which have the CTFA designation dimethicone, having a viscosity of from 5 to 100,000 centistokes at 25° C. These siloxanes are available commercially from the General Electric Company as the Viscasil series and from Dow Corning as the DC 200 series. The viscosity can be measured by means of a glass capillary viscometer as set out further in Dow Corning Corporation Test Method CTM004 Jul. 20, 1970.

Also suitable as an optional ingredient in compositions of the invention is polydiethyl siloxane.

The polyalkylaryl siloxanes which may also be optionally used in the compositions of the invention include polymethylpenyl polysiloxanes having a viscosity of from 15 to 65 centistokes at 25° C. These siloxanes are available commercially from the General Electric Company as SF 1075 methyl phenyl fluid or from Dow Corning as 556 Cosmetic Grade Fluid.

Also suitable optional ingredients are silicone gums, such as those described in U.S. Pat. No. 4,152,416 (Spitzer) and on the General Electric Silicone Rubber product Data Sheet SE 30, SE 33, SE 54, and SE 76. "Silicone gum" denotes polydiorganosiloxanes having a molecular weight of from 200,000 to 1,000,000, and specific examples include polydimethyl siloxane polymer, polydimethyl siloxane/diphenyl/methylvinylsiloxane copolymer, polydimethylsiloxane/methylvinylsiloxane copolymer and mixtures thereof.

Another optional ingredient is aminofunctional silicones which have the CFTA designation amodimethicone, such as Union Carbide TP 407 are also suitable for use in the compositions of the invention.

As noted above, high foaming anionic surfactants are important ingredients in the compositions of the invention. Preferred high foaming anionic surfactants include any of the anionic surfactants known or previously used in the art of skin and hair cleansers. An anionic surfactant is a necessary ingredient in the composition of the present invention because it effectively cleanses the skin and hair and generates a rich, stable foam level that consumers equate with cleaning efficiency.

Usually, the anionic surfactant includes a hydrophobic moiety, such as a carbon chain including about 8 to about 30 carbon atoms, and particularly about 12 to about 20 carbon atoms, and further includes a hydrophilic moiety, such as sulfate, sulfonate, carbonate, phosphate, or carboxylate. Often, the hydrophobic chain is etherified, such as with ethylene oxide, to impart a particular physical property, such as increased water solubility or reduced surface tension to the anionic surfactant.

The anionic surfactants are well known and have been widely used in the art of skin cleansers. Suitable anionic surfactants include, but are not limited to, compounds in the classes known as alkyl sulfates, alkyl ether sulfates, alkyl ethersulfonates, sulfate esters of an alkylphenoxy polyoxyethylene ethanol, alpha-olefin sulfonates, beta-alkoxy alkane sulfonates, alkylarylsulfonates, alkyl monoglyceride sulfates, alkyl monoglyceride sulfonates, alkyl carbonates, alkyl ether carboxylates, fatty acids, sulfosuccinates, sarcosinates octoxynol or nonoxynol phosphates, taurates, fatty taurides, fatty acid amido polyoxyethylene sulfates, isothionates or mixtures thereof. Additional anionic cleansing surfactants are listed in McCUTCHEON'S EMULSIFIERS AND DETERGENTS, 1993 ANNUALS, McCutcheon Division, MC Publishing Co. Glen Rock, N.J., pages 263–266, incorporated herein by reference. Numerous other anionic surfactants, and classes of anionic surfactants, are disclosed in Laughlin et al. U.S. Pat. No. 3,929,678 incorporated herein by reference.

Usually, the anionic surfactant is present in the composition as a neutralized salt in the form of a sodium, potassium, lithium, ammonium, alkylammonium or hydroxyalkyammonium salt, wherein the alkyl or hydroxyalkyl moiety has 1 to about 3 carbon atoms. The alkyl sulfates and alkyl ether sulfates are particularly effective classes of anionic surfactants. Examples of anionic surfactants useful in the compositions and methods of the invention include but are not limited to the ammonium, monethanolamine, diethanolamine, triethanolamine, isopropyl, sodium, potassium, lithium, and magnesium salts of lauryl sulfate, sodium laureth sulfate, dodecyl benzenesulfonate, laurel sulfosuccinate, lauryl ether sulfate, lauryl ether carbonate, lauryl sarcosinate, cocomethyl tauride, and sulfosuccinate half ester amide, or combinations thereof. Examples of especially useful anionic surfactants are sodium laureth sulfate, a lauryl ether sulfate salt and mixtures thereof.

Cationic polymers suitable for use in the compositions of the present invention are selected from the group consisting of polyquaternium 32, polyquaternium 3, cocodimonium hydroxypropyl hydrolyzed collagen, cocodimonium hydroxypropyl hydrolyzed hair keratin, cocodimonium hydroxypropyl hydrolyzed hair keratin, cocodimonium hydroxypropyl hydrolyzed keratin, cocodimonium hydroxypropyl hydrolyzed wheat protein, cocodimonium hydroxypropyl oxyethyl cellulose, guar hydroxypropyltrimonium chloride, lauryldimonium hydroxypropyl hydrolyzed collagen, lauryldimonium hydroxypropyl hydrolyzed wheat protein, lauryldimonium hydroxypropyl oxyethyl cellulose, polyquaternium 4, polyquaternium 10, polyquaternium 24, steardimonium hydroxyethyl cellulose, steardimonium hydroxypropyl hydrolyzed collagen, steardimonium hydroxypropyl hydrolyzed wheat protein, steardimonium hydroxypropyl oxyethyl cellulose, steardimonium hydroxyethyl hydrolyzed collagen, polymethacrylamidopropyl trimonium chloride, polyquaternium 2, polyquaternium 6, polyquaternium 7, polyquaternium 11, polyquaternium 16, polyquaternium 17, polyquaternium 18, polyquaternium 22, polyquaternium 27, polyquaternium 28, polyquaternium 31, polyquaternium 39, polyquaternium 41, polyquaternium 42, quaternium 80, and quaternized hydrolyzed wheatiprotein/dimethicone phosphocopolyol copolymer, As noted above, silicone copolyol sulfosuccinates are important ingredients in the compositions of the invention. Preferred silicone copolyol sulfosuccinates are prepared by reacting the ethoxylated polyether side chains of dimethicone copolyol with maleic anhydride to form a monoester. The side chains involved in this reaction are polymers or copolymers of ethylene or propylene oxide.

Other sulfosuccinates which may be used in the compositions of the invention include disodium dimethicone copolyol sulfosuccinate, dipotassium dimethicone copolyol sulfosuccinate, diammonium dimethicone copolyol sulfosuccinate, and triethanolamine dimethicone copolyol sulfosuccinate, Another important component of the compositions of the present invention is an emollient. Emollients help to maintain the soft, smooth and pliable appearance of skin. They function by their ability to remain on the skin surface or in the stratum corneum to act as a lubricant, to reduce flaking, and to improve the skin's appearance. Emollients can be oils, ethers of oils, acids of oils, or esters of oils. Emollients which may be used in compositions of the invention include all emollients which do not adversely affect the shampooing properties of the compositions of the invention. Examples of emollients include but are not limited to cocoate, and derivatives of cocoate such as PEG-7 glycerol cocoate, PEG-20 almond glycerides, PPG-1 ceteth 1, caprylic capric glycerides such as PEG 6 and 8, lanolin oil, milk lipids, jojoba oil, and hydrogenated or unhydrogenated castor oil. Other emollients which may be used in compositions of the invention include those listed in the International Cosmetic Ingredient Handbook, Third Edition, 1995, published by The Cosmetic Toiletry and Fragrance Association, pages 899–903, which is hereby incorporated by reference.

Amounts of ingredients in compositions of the invention are preferably present in the following ranges, based on 100% active:

Amounts of anionic surfactant range from 0.1% to 30%, more preferably 0.1% to 15%.

Amounts of cationic polymer range from 0.01% to 5%, more preferably 0.01% to 1%.

Amounts of silicone sulfosuccinate polymer range from 0.1% to 5%, more preferably 0.1% to 2%.

Amounts of emollient range from 0.01% to 30%, more preferably 0.01% to 10%.

As a cosmetically acceptable vehicle, it is particularly advantageous to use a carrier such as water. The vehicle may be present in amounts anywhere from about 99.5% to about 20%.

The most desirable physical forms for compositions of the invention are viscous liquids or lotions.

Further useful components of compositions of the invention are common cosmetic components and additives that can be included in the compositions of the invention as long as the basic properties of the compositions of the invention are not adversely affected. Such optional cosmetic components and additives include, but are not limited to, fragrance oils, nonionic surfactants, amphoteric surfactants fragrances, dyes, thickeners, hydrotropes, foam stabilizers, solubilizers, preservatives, water softening agents, acids alkalies, buffers, and the like. Likewise, the compositions can include other emulsifiers such as glycol stearate, viscosity enhancers such as carbopol, opacifiers such as mica and glycol stearate, conditioning agents, inorganic salts such as sodium chloride, humectants such as propylene glycol, and similar materials to provide the composition with desirable physical or esthetic properties. These optional components and additives usually are present in weight percentages of 0% to about 5% by weight each, and about 0.1 to about 20% by weight of the composition in total.

In addition, to improve skin mildness and composition esthetics, the compositions of the invention can optionally include an amphoteric surfactant in an amount of about 0.1 to about 5% by weight of the composition. Examples of amphoteric surfactants that can be included in the compositions of the invention are, but are not limited to betaines, hydroxypropylsultaines, amine oxides, n-alkylaminopropionates, n-alkylimino dipropionates, phosphobetaines, phosphitaines, imidazolines and mixtures thereof. Examples of specific amphoteric surfactants include, but are not limited to, coamidopropyl betaine, lauramidyl betaine, coc/oleamidopropyl betaine, coco betaine, oleyl betaine, coamidopropyl hydroxysultaines, tallowamidopropyl hydroxysultaines, (see U.S. Pat. No. 5,683, 683 which issued Nov. 4, 1997, and which is hereby incorporated by reference).

The compositions of the present invention also can include nonionic surfactants to help impart esthetic, physical or cleansing properties to the composition. For example, representative nonionic surfactants which can be included the compositions of the invention are esters and polyols of sugars, fatty alkanolamides, ethoxylated or propoxylated fatty alcohols, and the condensation products of ethylene oxide with long chain amines or amides. These nonionic surfactants, as well as numerous others not cited herein, are well known in the art and are fully described in the literature such as McCUTCHEON'S EMULSIFIERS AND DETERGENTS, 1993 ANNUALS, McCutcheon Division, MC Publishing Co. Glen Rock, N.J., pages 266–272, incorporated herein by reference.

In particular a nonionic alkanolamide can be included in the compositions of the invention to provide composition thickening and foam stability. (see U.S. Pat. No. 5,683, 683 which issued Nov. 4, 1997, and which is hereby incorporated by reference).

The compositions of the invention lather well and provide good cleansing as well as conditioning properties to the hair and skin.

Compositions of the invention are used by placing the composition into the hands and the lathering either in the hair or on the skin or both. Then the lather is rinsed off with water.

Alternatively, the compositions of the invention may be placed, for example, on a pouf, a wash cloth, or a natural or synthetic sponge, and lathered either in the hair or on the skin or both. Then the lather is rinsed off with water.

The following examples will more fully illustrate this invention. These examples are intended to illustrate the invention and not to limit it. All parts, percentages and proportions referred to herein and in the appended claims are by weight unless otherwise indicated.

Compositions of the invention are as follows. Compositions of the invention may be prepared as set forth below, or in a manner similar to that set forth below.

|   | Ingredient | Examples ||||||| 
|---|---|---|---|---|---|---|---|---|
|   |   | 1 | 2 | 3 | 4 | 5 | 6 | 7 |
| A. | water | 5 | 62.5 | 58.5 | 5 | 61 | qs. | qs |
| B. | anionic surfactant |   |   |   |   |   |   |   |
|   | sodium laureth(2)sulfate (25% active) | 50 | — | — | 50 | — | 55 | 55 |
|   | detergent blend* | — | 25 | 25 | — | 25 | — | — |

-continued

| Ingredient | | Examples | | | | | | |
|---|---|---|---|---|---|---|---|---|
| | | 1 | 2 | 3 | 4 | 5 | 6 | 7 |
| C. | Methocel 40-101 | .2 | .2 | .2 | .2 | .2 | .2 | .2 |
| D. | cationic polymer | | | | | | | |
| | Nhance 3196 (Aqualon) | .2 | .2 | .2 | — | — | .2 | .2 |
| | Merquat + 3330 (Calgon) | — | — | — | 2 | — | — | — |
| | Polymer JR 30M (Union Carbide) | — | — | — | — | .2 | — | — |
| | propylene glycol | — | — | — | — | — | .5 | — |
| E. | pH adjuster to pH 5.0–6.0 | qs. | qs. | qs. | qs. | qs | .03 | qs |
| F. | secondary surfactants | | | | | | | |
| | cocamidopropylbetaine (30% active) | 6 | — | — | 6 | 1.5 | 6.0 | 6.0 |
| | ammonium cocoyl isethionate (30% active) | 3 | — | 3 | 3 | 3 | 3 | 3 |
| | sodium methyl cocoyl taurate | — | 5 | — | — | — | — | — |
| G. | disodium dimethicone copolyol sulfosuccinate (50% active) | 1 | 1 | 2 | 1 | .5 | 1.0 | 1.0 |
| H. | Carbopol 980 | .5 | — | — | — | — | .5 | .5 |
| I. | water | 24.5 | — | — | — | — | 24.5 | 24.5 |
| J. | silicone emulsion | | | | | | | |
| | Dow Corning 1784 | 4 | — | — | — | — | 4.0 | 4.0 |
| | Dow Corning 2-1870 | — | — | 5 | 5 | 2.5 | — | — |
| K. | emollient | | | | | | | |
| | PEG-7 glyceryl cocoate | 1.5 | — | 1.5 | 1.5 | 1.0 | 1.5 | 1.5 |
| | glycerine | — | 1 | — | — | — | — | — |
| | myristyl propionate | — | .5 | — | — | — | — | — |
| L. | pearlizing agent | | | | | | | |
| | Timiron MP-30 (Rona) | .2 | .2 | .2 | .2 | .2 | .2 | .2 |
| | cocamidopropylbetaine (30% active) | — | — | — | — | — | .7 | .7 |
| M. | preservatives | qs. | qs. | qs. | qs. | qs. | $.2^2$ $.1^3$ $.05^4$ | qs. |
| N. | fragrance | qs. | qs. | qs. | qs. | qs. | .65 | qs. |
| O. | water | qs. | qs. | qs. | qs. | qs. | qs. | qs. |
| P. | pH adjuster to pH 5.5–6.5 | qs. | qs. | qs. | qs. | qs. | $.35^5$ | qs. |
| Q. | Sodium Chloride to viscosity 4000–9000 cps | qs. | qs. | qs. | qs. | qs. | .9 | qs. |

*ammonium lauryl sulfate (30%), ammonium laureth(1) sulfate (23%), lauramide DEA (10%), ammonium xylene sulfonate (3%), PEG-600 (0.45%), water to make 100%.
[1]citric acid (50% active)
[2]versene 100
[3]DMDM Hydantoin
[4]Kathon CG
[5]NaOH (50% active)

1. To A, add B.
2. Add C.
3. Add D. In Example 6 add D into propylene glycol, and then add into above.
4. Mix until homogenous.
5. Adjust pH to 5–6 with E. Mix until homogenous.
6. Add F and mix well.
7. Add G and mix well.
8. In examples 1, 6 and 7, add H premixed in I, and mix well.
9. Add J, K, L, M, and N, mixing well after each addition.
10. With 0, q.s. to 100%.
11. Adjust pH with P to pH 5.5–6.5.
12. Adjust viscosity with Q to 4000–9000 cps (Brookfield spindle 4, speed 20).

The foregoing descriptions and examples illustrate selected embodiments of the present invention and in light thereof various modifications will be suggested to one skilled in the art, all of which are within the sprit and purview of this invention.

What is claimed and desired to be secured by Letters Patent is:

1. A composition for cleansing, conditioning, and moisturizing the skin and hair which comprises:

| Ingredient | Wt. % |
|---|---|
| Water | 5 |
| Sodium Laureth (2) Sulfate (25% active) | 50 |
| Hydroxypropyl Methylcellulose | .2 |
| Guar Gum, 2-Hydroxy 3(Trimethylammonio) Propyl Ether Chloride | .2 |
| pH Adjuster to pH 5.0–6.0 | Qs. |
| Cocamidopropyl Betaine (30% Active) | 6 |
| Ammonium Cocoyl Isethionate (30% Active) | 3 |
| Disodium Dimethicone Copolyol Sulfosuccinate (50% Active) | 1 |
| Carbomer | .5 |
| Water | 24.5 |
| Dimethiconol and Tea-Dodecyl Benzenesulfonate | 4 |
| PEG-7 Glycerol Cocoate | 1.5 |
| Mica and Titanium Dioxide | .2 |
| Preservatives | Qs. |
| Fragrance | Qs. |
| Water | Qs. |
| pH Adjuster to pH 5.5–6.5 | Qs. |
| Sodium Chloride to Viscosity 4000–9000 CPS | Qs. |

2. A composition for cleansing, conditioning, and moisturizing the skin and hair which comprises:

| Ingredient | Wt. % |
|---|---|
| Water | 62.5 |
| Detergent Blend* | 25 |
| Hydroxypropyl Methylcellulose | .2 |
| Guar Gum, 2-Hydroxy 3(Trimethylammonio) Propyl Ether Chloride | .2 |
| pH Adjuster to pH 5.0–6.0 | Qs. |
| Sodium Methyl Cocoyl Taurate | 5 |
| Disodium Dimethicone Copolyol Sulfosuccinate (50% Active) | 1 |
| Glycerine | 1 |
| Myristyl Propionate | .5 |
| Mica and Titanium Dioxide | .2 |
| Preservatives | Qs. |
| Fragrance | Qs. |
| Water | Qs. |
| pH Adjuster to pH 5.5–6.5 | Qs. |
| Sodium Chloride to Viscosity 4000–9000 CPS | Qs. |

*Ammonium Lauryl Sulfate (30%), Ammonium Laureth(1) Sulfate (23%), Lauramide DEA.

3. A composition for cleansing, conditioning, and moisturizing the skin and hair which comprises:

| Ingredient | Wt. % |
|---|---|
| Water | 58.5 |
| Detergent Blend* | 25 |
| Hydroxypropyl Methylcellulose | .2 |
| Guar Gum, 2-Hydroxy 3(Trimethylammonio) Propyl Ether Chloride | .2 |
| pH Adjuster to pH 5.0–6.0 | Qs. |
| Ammonium Cocoyl Isethionate (30% Active) | 3 |
| Disodium Dimethicone Copolyol Sulfosuccinate (50% Active) | 2 |
| Dimethiconol and Tea-Dodecyl Benzenesulfonate and Laureth-23 | 5 |
| PEG-7 Glyceryl Cocoate | 1.5 |
| Mica and Titanium Dioxide | .2 |
| Preservatives | Qs. |
| Fragrance | Qs. |
| Water | Qs. |
| pH Adjuster to pH 5.5–6.5 | Qs. |
| Sodium Chloride to Viscosity 4000–9000 CPS | Qs. |

*Ammonium Lauryl Sulfate (30%), Ammonium Laureth(1) Sulfate (23%), Lauramide DEA.

4. A composition for cleansing, conditioning, and moisturizing the skin and hair which comprises:

| Ingredient | Wt. % |
|---|---|
| Water | 5 |
| Sodium Laureth(2) Sulfate (25% Active) | 50 |
| Hydroxypropyl Methylcellulose | .2 |
| Polyquaternium-39 | 2 |
| pH Adjuster to pH 5.0–6.0 | Qs. |
| Cocamidopropylbetaine (30% Active) | 6 |
| Ammonium cocoyl Isethionate (30% Active) | 3 |
| Disodium Dimethicone Copolyol Sulfosuccinate (50% Active) | 1 |
| Dimethiconol and Tea-Dodecyl Benzenesulfonate and Laureth-23 | 5 |
| PEG-7 Glyceryl Cocoate | 1.5 |
| Mica and Titanium Dioxide | .2 |
| Preservatives | Qs. |
| Fragrance | Qs. |
| Water | Qs. |
| pH Adjuster to pH 5.5–6.5 | Qs. |
| Sodium Chloride to Viscosity 4000–9000 CPS | Qs. |

5. A composition for cleansing, conditioning, and moisturizing the skin and hair which comprises:

| Ingredient | Wt. % |
|---|---|
| Water | 61 |
| Detergent Blend* | 25 |
| Hydroxypropyl Methylcellulose | .2 |
| Polyquaternium-10 | .2 |
| pH Adjuster to pH 5.0–6.0 | Qs. |
| Cocamidopropylbetaine (30% Active) | 1.5 |
| Ammonium Cocoyl Isethionate (30% Active) | 3 |
| Disodium Dimethicone Copolyol Sulfosuccinate (50% Active) | .5 |
| Dimethiconol and Laureth-23 and Tea-Dodecyl Benzenesulfonate | 2.5 |
| Mica and Titanium Dioxide | .2 |
| Preservatives | Qs. |
| Fragrance | Qs. |
| Water | Qs. |
| pH Adjuster to pH 5.5–6.5 | Qs. |
| Sodium Chloride to Viscosity 4000–9000 CPS | Qs. |

*Ammonium Lauryl Sulfate (30%), Ammonium Laureth(1) Sulfate (23%), Lauramide DEA.

6. A composition for cleansing, conditioning, and moisturizing the skin and hair which comprises:

| Ingredient | Wt. % |
|---|---|
| Water | Qs. |
| Sodium Laureth(2)Sulfate (25% Active) | 55 |
| Detergent Blend* | 25 |
| Hydroxypropyl Methylcellulose | .2 |
| Guar Gum, 2-Hydroxy 3(Trimethylammonio) Propyl Ether Chloride | .2 |
| pH Adjuster to pH 5.0–6.0 | Qs. |
| Cocamidopropylbetaine (30% Active) | 6.0 |
| Ammonium Cocoyl Isethionate (30% Active) | 3 |
| Disodium Dimethicone Copolyol Sulfosuccinate (50% Active) | 1 |
| Carbopol 980 | .5 |
| Water | 24.5 |
| Dimethiconol and Tea-Dodecyl Benzenesulfonate | 4 |
| PEG-7 Glyceryl Cocoate | 1.5 |
| Mica and Titanium Dioxide | .2 |
| Cocamidopropylbetaine (30% Active) | .7 |
| Preservatives | Qs. |
| Fragrance | Qs. |
| Water | Qs. |
| pH Adjuster to pH 5.5–6.5 | Qs. |
| Sodium Chloride to Viscosity 4000–9000 CPS | Qs. |

*Ammonium Lauryl Sulfate (30%), Ammonium Laureth(1) Sulfate (23%), Lauramide DEA.

7. A method for cleansing, conditioning, and moisturizing the skin and hair which comprises placing a composition of claim 1, 2, 3, 4 or 5 into the hands, lathering the skin and/or hair and rinsing off the lather with water.

8. A method for cleansing, conditioning, and moisturizing the skin and hair which comprises placing a composition of claim 1, 2, 3, 4 or 5 on a pouf, a wash cloth, or a natural or synthetic sponge, and lathering the hair and/or skin and rinsing off the lather with water.

* * * * *